United States Patent
Nonami et al.

(10) Patent No.: US 6,825,155 B2
(45) Date of Patent: Nov. 30, 2004

(54) COMPOSITION FOR DEODORIZATION AND DECONTAMINATION OF DENTAL PRODUCT

(75) Inventors: Toru Nonami, Nagoya (JP); Takayuki Kumagai, Nisshin (JP); Hiroshi Taoda, Nagoya (JP)

(73) Assignee: National Institute of Advanced Industrial Science and Technology, Tokyo-to (JP)

(*) Notice: Subject to any disclaimer, the term of this patent is extended or adjusted under 35 U.S.C. 154(b) by 0 days.

(21) Appl. No.: 10/048,414

(22) PCT Filed: May 30, 2001

(86) PCT No.: PCT/JP01/04547

§ 371 (c)(1),
(2), (4) Date: Apr. 4, 2002

(87) PCT Pub. No.: WO01/91701

PCT Pub. Date: Dec. 6, 2001

(65) Prior Publication Data

US 2002/0169073 A1 Nov. 14, 2002

(30) Foreign Application Priority Data

May 31, 2000 (JP) .......................... 2000-163679

(51) Int. Cl.[7] .............................. A61K 6/04; A61K 7/16
(52) U.S. Cl. ..................... 510/116; 510/161; 424/49; 424/50; 424/53; 424/57; 424/603; 424/613; 433/216
(58) Field of Search .................... 510/116, 161; 424/49, 50, 53, 57, 403, 413; 106/35, 443, 444; 523/115; 433/216; 428/403, 404

(56) References Cited

U.S. PATENT DOCUMENTS 5,981,425 A * 11/1999 Taoda et al. ............. 502/208
6,090,736 A * 7/2000 Taoda et al. ............. 502/5

FOREIGN PATENT DOCUMENTS

| JP | 5-32518 | 2/1993 |
| JP | 6-254139 | 9/1994 |
| JP | 10-17847 | 1/1998 |
| JP | 10-244166 | 9/1998 |
| JP | 10-273412 | * 10/1998 |
| JP | 2000-44449 | 2/2000 |
| JP | 2000-119957 | * 4/2000 |
| JP | 2000-126611 | 5/2000 |
| JP | 2000-239823 | 9/2000 |
| JP | 2000-344640 | 12/2000 |
| JP | 2001-114658 | 4/2001 |
| WO | WO 99/33566 | 7/1999 |

OTHER PUBLICATIONS

Translation for JP 2001–114658.*

Translation for 2000–344640.*

* cited by examiner

*Primary Examiner*—C. Melissa Koslow
(74) *Attorney, Agent, or Firm*—Nixon & Vanderhye P.C.

(57) ABSTRACT

A dental resin material mixed with a composition containing, as a maincomponent, titanium dioxide whose surface has been partly coated with apatite. In the dental resin material, it is preferable that anatase-, rutile-, brookit-type titanium dioxide or a mixture of these components is used as the titanium dioxide. The apatite for partial coating of titanium dioxide is produced by immersing powdery titanium dioxide in a pseudo body fluid and stirring the immersed titanium dioxide approximately at the same temperature as a human body temperature, i.e., 36° C. In this instance, it is important that the apatite is deposited in the form of platy crystals of less than 2 mm in thickness to cover 0.001–10% of the surface of titanium dioxide.

10 Claims, 3 Drawing Sheets

Upper jaw                Lower jaw

COMPOSITION FOR DEODORIZATION AND DECONTAMINATION OF DENTAL PRODUCT

TECHNICAL FIELD

The present invention relates to a composition containing, as a main component, titanium dioxide effective for enhancing deodorization, decontamination, removal of germ and cleaning properties of dental products such as a crown, a denture, an orthodontia bed, a mouthpiece or the like made of acrylic resin composition. More particularly, the present invention relates to a compounding agent essentially consisting of a composition containing, as a main component, titanium dioxide suitable for enhancing deodorization, decontamination, removal of germ and cleaning properties of dental products made of kneaded acrylic resin composition, a coating agent essentially consisting of a composition containing, as a main component, titanium dioxide to be coated on a surface of a dental product in use for enhancing deodorization, decontamination, removal of germ and cleaning properties of the dental product, and a detergent essentially consisting of a composition containing, as a main component, titanium dioxide suitable for cleaning a dental product.

TECHNICAL BACKGROUND

As a dental prosthesis such as a denture, an orthodontia bed used in general in a conventional dental treatment is contaminated by plaque gradually adhered thereto in a mouth, it is needed to daily wash the dental prosthesis by mechanical washing such as brushing or use of a denture detergent. Although the surface contamination of the denture can be removed by the mechanical washing or use of the denture detergent, removal of contaminant and coloring matter absorbed in the denture is difficult. For this reason, there has been proposed a method of coating a denture, an orthodontia bed, a denture repair material, a mouthpiece, etc. with a dental resin composition mixed with deodorant ingredients, decontamination ingredients or the like.

As a dental resin composition of this kind used in the coating treatment, proposed in Japanese Patent Laid-open Publication No. 5-32516 is a germicidal thermosetting resin composition mixed with fine particles of titania deposited therein with a metal for effecting photoelectrochemical sterilization function of titania. As a deodorant dental resin, proposed in Japanese Patent Laid-open Publication No. 10-273412 is a deodorant dental resin composition containing ester monomer of methacrylic acid, anatase-type titanium dioxide ($TiO_2$) and polymerization initiator. With regard to the dental resin composition, it is reported that a dental material made of the dental resin composition has a resolution effective for deodorizing a foul odor and contaminants absorbed therein in a mouth under irradiation of light and that a foul odor unremoved in use of a conventional detergent can be removed when a denture made of the dental resin composition is washed under fluorescent light or sunbeam.

Although the germicidal thermosetting resin and the deodorant dental resin composition are utilized to effect activated photocatalysis of titanium dioxide, these dental resin compositions are decomposed due to activated photocatalysis of titanium dioxide, resulting in deterioration in strength and changes in color and quality. For this reason, the dental resin composition may not be used for a long period of time.

In addition, the following problems will occur in use of the dental acrylic resin material in a mouth due to a water-absorption property and an oil-absorption property of the material.

1) Unpleasant feel caused by permeation of odor
2) Spoil of beauty caused by adherence of coloring matter.
3) Adherence of tartar, residue of foods, etc.
4) Breeding of germs caused by impurities.

It is difficult to solve the problems by mere mixture of titanium dioxide with the foregoing dental resin material.

BRIEF SUMMARY OF THE INVENTION

To solve the problems discussed above, a primary object of the present invention is to provide a dental resin material, a dental resin product, a compounding agent, a coating agent and a detergent capable of enhancing sterilization and deodorization properties caused by activated photocatalysis of titanium dioxide and of restraining decomposition, deterioration in strength and changes in color and quality of the dental resin material.

To attain the object, the inventors noticed the facts that apatite such as apatite hydroxide, calcium phosphate or the like has a restraint function of deterioration of the dental resin material and an absorption function of contaminants such as residue of foods and that sterilization and deodorization functions are effected by activated photo-catalysis of titanium dioxide. Based on the above observation, the inventors developed a composition effective for deodorization and decontamination of dental products, which contains apatite effective for restraining deterioration of the resin caused by titanium dioxide and for absorbing contaminants in use of the dental products in a mouth and titanium dioxide effective for sterilizing contaminants absorbed in the apatite and deodorizing foul odor matters by activated photocatalysis during washing of the dental products under irradiation of light.

According to the present invention, there are provided the following dental resin material, compounding agent, coating agent and detergent.

1) A dental resin material mixed with a composition containing, as a main component, titanium dioxide whose surface has been partly coated with apatite.
2) A dental resin product provided therein with a composition containing, as a main component, titanium dioxide whose surface has been partly coated with apatite.
3) A compounding agent containing, as a main component, titanium dioxide whose surface has been partly coated with apatite to be mixed with a dental resin material for use.
4) A coating agent containing, as a main component, titanium dioxide whose surface has been partly coated with apatite to be coated on the surface of a dental resin product in use.
5) A detergent containing, as a main component, titanium dioxide to be used for washing of a dental resin product.
6) A detergent containing, as a main component, titanium dioxide whose surface has been partly coated with apatite to be used for washing of a dental resin product.
7) A detergent of a dental resin product in the form of an aqueous solution in which an adjustment agent consisting of acid, peroxide, enzyme or a compound of these components is dispersed and mixed with titanium dioxide whose surface has been partly coated with apatite.

In actual practice of the present invention, it is desirable that anatase-, rutile-, brookite-type titanium dioxide or a mixture of these components is used as the titanium dioxide for the foregoing dental resin material, dental resin product, compounding agent, coating agent or detergent.

The apatite for partial coating of titanium dioxide is produced by immersing powdery titanium dioxide in an amount of a pseudo body fluid and stirring the immersed titanium dioxide approximately at the temperature as the human body temperature, i.e., at about 36° C. In this instance, it is important that the apatite is deposited in the form of platy crystals of less than 2 mm in thickness to cover 0.001–10 wt. % of the surface of titanium dioxide.

In the production process of the dental resin material, an optimum result was obtained when a mixture amount of the titanium dioxide partly coated with the apatite is adjusted to 0.001–20 wt. %, desirably to 0.01–20 wt. % of the dental resin such as dental acryl resin or the like.

In the production process of the detergent, it is desirable that phosphoric acid, sodium pyrophosphric acid or hydrogen peroxide is used as the adjustment agent. In this instance, a desired result was obtained when the amount of phosphoric acid was adjusted to 0.001–100 wt. %, preferably to 0.01–10 wt. %, the amount of sodium pyrophosphoric acid is adjusted to 0.001–20 wt. %, preferably to 0.01–10 wt. % or the amount of hydrogen peroxide is adjusted to 0.1–36 wt. %, preferably to 2.0–7 wt. %.

The dental resin material of the present invention is most suitable for production of a crown, a denture, a mouthpiece or the like and is used in necessity as a tooth restoration material, a prosthesis material, a denture stabilizer, a model material, an orthodontia material or the like. The detergent of the present invention is most effective to decontaminate and deodorize the dental resin product when it is used to wash the resin product under irradiation of fluorescent lamp or sun beam thereby to clean the resin product without causing any change in quality and color.

DETAILED DESCRIPTION OF EXEMPLARY EMBODIMENTS

Figure 1:
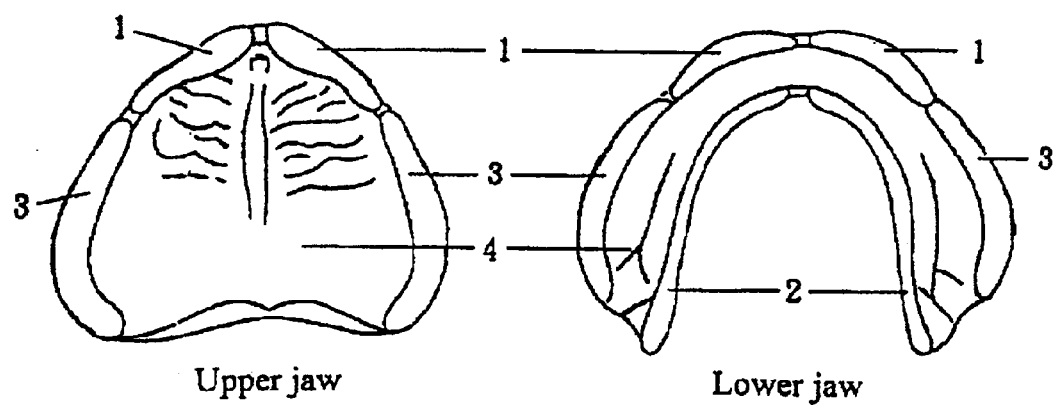
FIG. 1 illustrates a dental resin material of the present invention embedded in the entire surface and peripheral edge portions of a denture.

A dental resin material of the present invention is in the form of an acrylic resin material mixed with a composition containing, as a main component, titanium dioxide whose surface has been partly coated with apatite. The dental resin material is adapted for use as a material of a dental product such as a denture, a mouthpiece or the like, a tooth restoration material, a prosthesis material, a denture stabilizer, a model material, an orthodontia material or the like. In the dental resin material, ester monomer of methacrylic acid, alkyl methacrylate, and other methacrylate are used as the acrylic resin material. In necessity, an organic filler of polymethyl methacrylate, an inorganic filler of silica powder, a polymerization prohibiter such as hydroquinone, an oxidation stabilizer, an ultraviolet absorbent, a pigment, a dyestuff, a solvent, a dispersant, fibers, etc. may be contained in the acrylic resin material.

In the dental resin material of the present invention, apatite hydoxide ($Ca_{10}(OH)_2(PO_4)_6$) or phosphoric acid calcium is used as the apatite, and anatase-, rutile-, brookite-type titanium dioxide or fine powder of a mixture of these components is used as the titanium dioxide. In this instance, the fine powder is prepared in particle diameter less than 10 $\mu$m, preferably less than 0.1 $\mu$m and may be deposited in a biocompatible metal, in necessity.

In actual practice of the present invention, the apatite is produced by immersing powdery titanium dioxide in an amount of a pseudo body fluid and stirring the immersed titanium dioxide approximately at the same temperature as the human body temperature, i.e., at about 36° C. In this instance, it is desirable that the apatite is prepared in the form of platy crystals of less than 2 mm in thickness to increase an absorption area thereof, and it is important that the surface of titanium dioxide is partly covered with the apatite. In an experiment carried out by the inventors, an optimum result was obtained when 0.001–20%, preferably 0.001–10% of the surface of titanium dioxide was covered with the apatite. In addition, it is desirable that the mixing ratio of the titanium dioxide partly covered with the apatite to the resin material is adjusted to 0.001–20 wt. %, preferably to 0.01–5 wt. %. If the mixing ratio of the titanium dioxide to the resin material is less than 0.001 wt. %, the apatite becomes ineffective. If more than 20 wt. %, the resin material is deteriorated in strength, and there will occur unpleasant feel in an attachment membrane.

In use of the dental resin material prepared in the foregoing manner, the resin material is embedded in a portion of a dental product used in a mouth or coated on a surface of the dental product by brush or pasted in the form of a membrane to an appropriate portion of the dental product. With such usage, the dental resin material of the present invention is useful to repair a false tooth accustomed in use.

A dental article such as a denture, a crown, a mouthpiece or the like made of the resin material can be cleaned by washing with city service water under irradiation of light so that contaminants and foul odor matters absorbed in the apatite are removed by activated photo-catalysis of the titanium dioxide contained in the dental product. Thus, in use of the dental product made of the dental resin material, it is able for a long period of time to eliminate unpleasant feel caused by soaked odor, presence of coloring matters, etc., to prevent adhesion of tartar and residue of foods and to remove germs adhered to the dental product.

According to one aspect of the present invention, there is provided a detergent for a dental product containing, as a main component, titanium dioxide or titanium dioxide partly covered with the apatite. In a practical embodiment of the present invention, the detergent is added with acid, peroxide, enzyme or a mixture of these components to prepare an aqueous solution containing dispersed powder of the detergent. In washing, a dental product made of conventional acrylic resin is immersed in and washed with the prepared aqueous solution under irradiation of light. Alternatively, the dental product is coated with the prepared aqueous solution and washed under irradiation of light. As a result, contaminants such as plaque difficult to remove with a conventional detergent can be washed out in a simple manner to eliminate unpleasant odor of the dental product.

In addition, it is preferable that the acid used in the detergent is selected from a group consisting of phosphoric acid, pyrophosphoric acid, poly-phosphoric acid, tripolyphosphoric acid, acetic acid, citric acid, tartaric acid, malic acid, formic acid, gluconic acid, silicic acid, succinic acid, oxalic acid, sorbic acid, hydrochloric acid, sulfuric acid, lactic acid, folic acid and butyric acid. In use of phosphoric acid or pyrophosphoric acid, a desired result was obtained when phosphoric acid was adjusted in amount to 0.001–100 wt. %, preferably 0.01–10 wt. % or when pyrophosphoric acid was adjusted in amount to 0.001–20 wt. %, preferably 0.01–10 wt. %. In use of hydrogen peroxide, a desired result was obtained when an addition amount of hydrogen peroxide was adjusted to 0.1–36 wt. %, preferably 2.0–7 wt. %.

In the washing process, sunbeam, fluorescent light, a light-emitting diode, a UV light, a black light, a semiconductor laser, a white-heat light, a quartz lamp, a mercury lamp, a xenon lamp, a heat-generation lamp, a halogen lamp, a cold-cathode lamp, etc. may be selectively used as a source of light.

EXAMPLES

The dental resin material and detergent of the present invention were used as in the following examples.

Example 1

A dental resin material was prepared by 100 parts of acrylic resin powder (made by GC Co. Ltd.: Akron) added with 0.001–1.0 wt. % powder of titanium dioxide partly covered with the apatite. As shown in FIG. 1, the prepared dental resin material was embedded in a denture at portions indicated with a reference numeral 4. Additionally, another dental resin material was prepared by 100 parts of the acryl resin powder added with 0.001–20 wt. % powder of titanium dioxide partly covered with the apatite. As shown in FIG. 1, the prepared dental resin material was embedded in the denture at portions indicated with reference numerals 1, 2 and 3. In this example, titanium dioxide of 10 nm in particle diameter (made by Showa Denko Co. Ltd.) was used as the titanium dioxide, and the apatite was prepared in particle diameter of 0.5 μm.

When the denture was washed with fresh water, residue of foods and contaminants were removed from the denture and became non-adhesive to the denture. In addition, undesired color and adhered matters became removable at portions of the denture indicated with the reference numerals 1, 2 and 3.

Example 2

Figure 2:
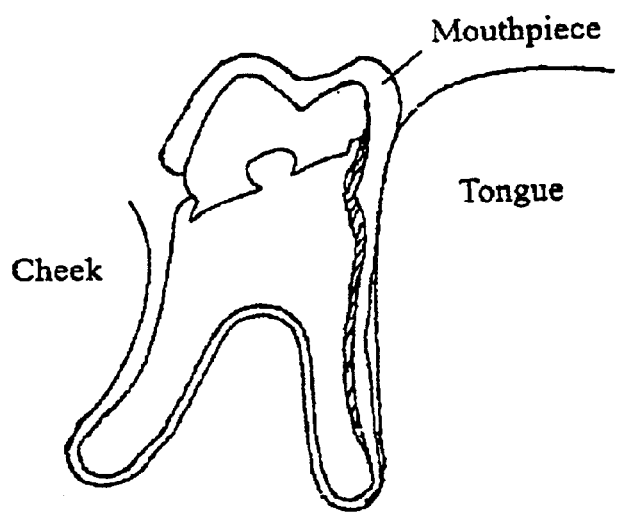
FIG. 2 illustrates a dental resin material of the present invention embedded in an internal surface of a mouthpiece.

A dental resin material was prepared by 100 parts of acrylic resin powder (made by CC Co. Ltd.: Akron) added with 0.001–20 wt. % powder of titanium dioxide partly covered with the apatite. As shown in FIG. 2, the dental resin material was embedded in a tongue side oblique portion of a mouthpiece. As a result, contaminants and foul odor adhered to a tusk surface of the mouthpiece were removed by washing.

Example 3

Figure 3:
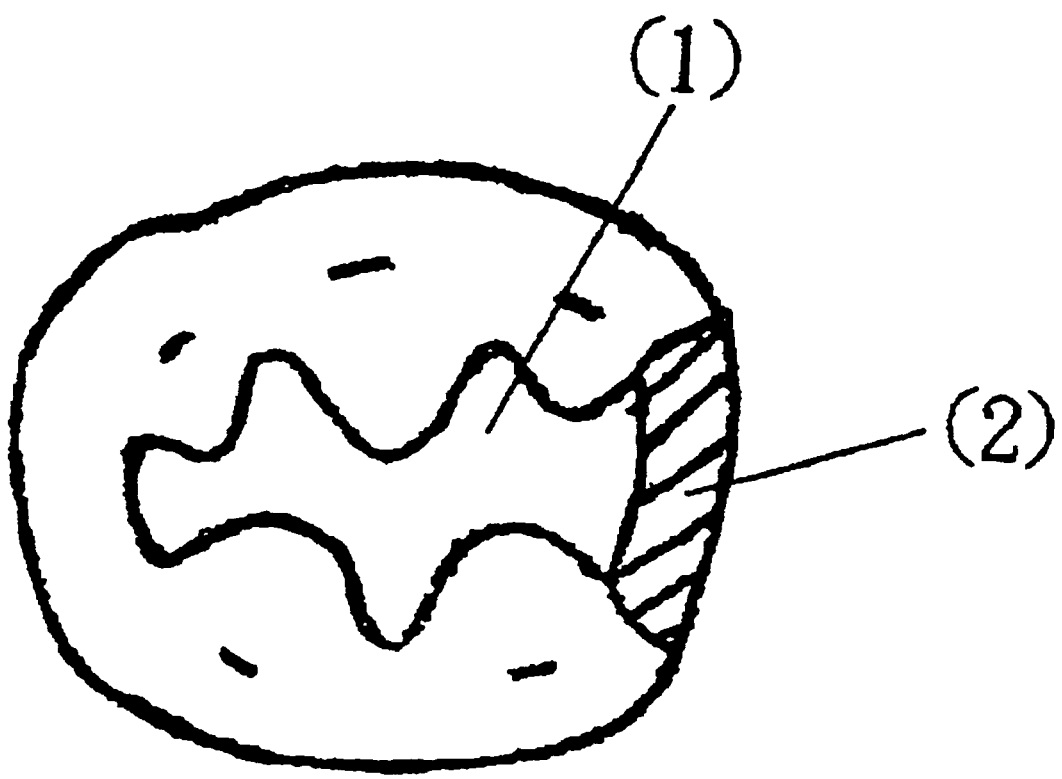
FIG. 3 illustrates a dental resin material of the present invention embedded and cemented as an inlay in a decayed cavity of a tooth.

A dental resin material was prepared by 100 parts of heat-polymerization hard resin (made by Ibokura Co. Ltd.) added with 0.001–1.0 wt. % powder of titanium dioxide partly covered with the apatite. As shown in FIG. 3, the dental resin material was embedded and cemented as an inlay (2) in a decayed cavity (1) of a human tooth. As a result, adjacent teeth and tooth stem portions were cleaned by washing in a simple manner.

Example 4

Figure 4:
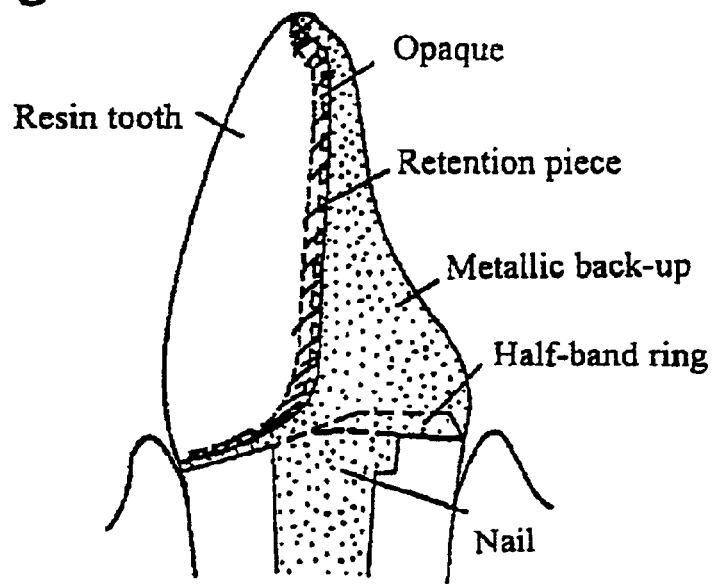
FIG. 4 illustrates a dental resin material embedded and secured in an opaque portion of a tooth.

The dental resin material used in Example 3 was embedded in an oblique portion of a front crown of resin as shown in FIG. 4. As a result, adhesion of coloring matters between a metal portion and a tooth of resin was reduced.

Example 5

Figure 5:
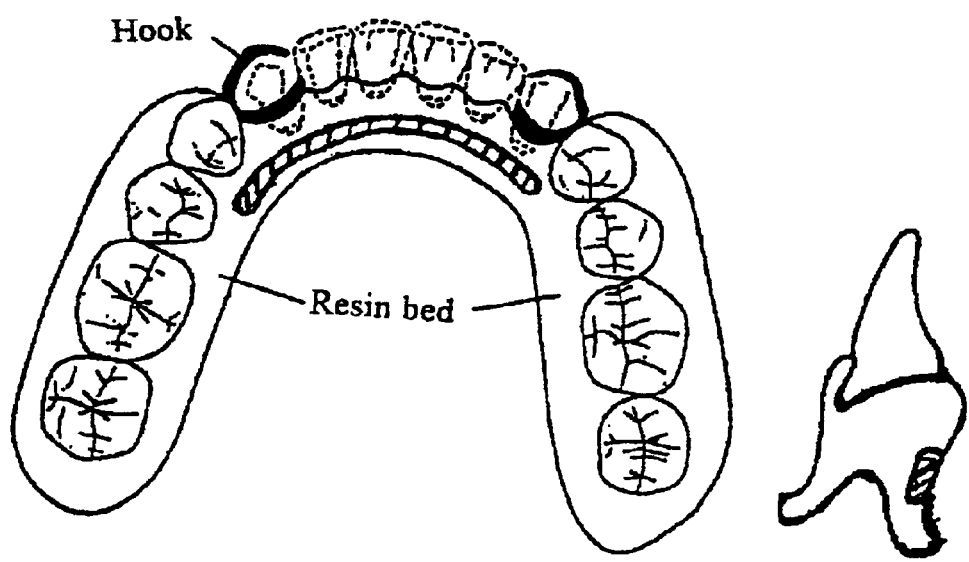
FIG. 5 illustrates a dental resin material embedded in a partial denture being used.

The dental resin material used in Example 1 was embedded in a recess formed in a tongue side oblique portion of a partial denture being used as shown in FIG. 5. As a result, residue of foods became non-adhesive to a tongue side surface of the denture.

Example 6

In this example, four kinds of resin materials were prepared as follows. A first resin material (1) was prepared by powder of clear resin (made by Mitsubishi Kasei Co. Ltd.) added with 1 wt. % powder of titanium dioxide partly covered with the apatitte. A second resin material (2) was prepared by the powder of clear resin added with 5 wt. % powder of the titanium dioxide. A third resin material (3) was prepared by the powder of clear resin added with only titanium dioxide. A fourth resin material (4) was prepared by only the powder of clear resin. These resin materials were immersed in a mixture solution of soy sauce and cocoa for a one month to investigate a change of the resin materials. As a result, it was observed that any odor and contaminants were not adhered to the first, second and third resin materials (1), (2) and (3) whereas the fourth resin material (4) was changed in color and harmed with foul odor adhered thereto.

Example 7

In this example, a denture of resin used in a mouth was washed with an aqueous solution of photo-catalyst shown in the following table 1. In this instance, 1 g of titanium dioxide was immersed in 1 liter of darbeco-PBS (±) for one hour to extract apatite of less than 1 nm in thickness on the surface of titanium dioxide. In the case of coating, 0.9 wt. % lavonite was added as a thickener to each aqueous solution. Thus, the dental resin material prepared in the foregoing manner was immersed in the aqueous solution or coated with the aqueous solution and washed under irradiation of light. A result of the washing is shown in the following table 1. In the table, the character X represents non-removal of odor and contaminants, the character Δ represents non-removal of contaminants, the character ○ represents removal of odor and usual contaminants, and the character ◉ represents removal of foul odor, tar of tobacco, tartar and heavy contaminants.

TABLE 1

| | | Result | | | |
|---|---|---|---|---|---|
| | | Coating | Black-light | | Sunbeam |
| Photo-catalyst | $H_2O_2$ (%) | 1 hour | 1 hour | 4 hours | 12 hours | 12 hours |
| anatase-type $TiO_2$ 5 nm | | | | | | |
| 0.001% | 0 | Δ | ○ | ○ | ○ | ○ |
| 0.01% | 3 | ○ | ○ | ○ | ◉ | ○ |
| 0.05% | 6 | ○ | ◉ | ◉ | ◉ | ○ |
| anatase-type $TiO_2$ 5 nm | | | | | | |
| 0.06% | 0 | Δ | ◉ | ◉ | ◉ | ○ |
| 0.1% | 3 | ◉ | ◉ | ◉ | ◉ | ○ |
| 1.0% | 6 | ◉ | ◉ | ◉ | ◉ | ◉ |

TABLE 1-continued

| Photo-catalyst | H₂O₂ (%) | Coating 1 hour | Black-light 1 hour | Black-light 4 hours | Black-light 12 hours | Sunbeam 12 hours |
|---|---|---|---|---|---|---|
| anatase-type TiO₂ 5 nm | | | | | | |
| 2.0% | 0 | ○ | ○ | ○ | ◎ | ○ |
| 5.0% | 3 | ◎ | ○ | ○ | ○ | ○ |
| 10.0% | 6 | ◎ | ◎ | ◎ | ◎ | ◎ |
| TiO₂ Coated with apatite | | | | | | |
| 0.001% | 0 | ○ | ○ | ◎ | ◎ | ○ |
| 0.05% | 3 | ◎ | ◎ | ◎ | ◎ | ○ |
| 2.0% | 6 | ◎ | ◎ | ◎ | ◎ | ◎ |
| non | 0 | X | X | X | X | X |
| | 3 | X | X | X | X | X |
| | 6 | X | X | X | X | X |
| Goods on the market | — | X | Δ | X | X | X |

Example 8

In this example, a denture of resin used in a mouth was washed with a phosphoric acid solution of photocatalyst shown in the following table 2. In this instance, 1 g of titanium dioxide was immersed in 1 liter of darbeco-PBS (±) for one hour to extract apatite of less than 1 nm in thickness on the surface of titanium dioxide. In the case of coating, 0.9 wt. % lavonite was added as a thickener to each aqueous solution. Thus, the dental resin material prepared in the foregoing manner was immersed in the phosphoric acid solution or coated with the phosphoric acid solution and washed under irradiation of light. A result of the washing is shown in the following table 2. In the table, the character X represents no-n-removal of odor and contaminants, the character Δ represents non-removal of contaminants, the character ○ represents removal of odor and usual contaminants, and the character ◎ represents removal of foul odor, tar of tobacco, tartar and heavy contaminants.

Based on the examples described above, it has been observed that in use of the dental resin material or detergent of the present invention, the contaminant absorption property of the apatite and the activated photocatalysis of titanium dioxide are useful to remove contaminants in a mouth in a simple manner thereby to prevent secondary caries.

TABLE 2

| Photo-catalyst | Phospholic aicd (%) | Coating 1 hour | Black-light 1 hour | Black-light 3 hours | Black-light 6 hours | Sunbeam 1 hour | Sunbeam 3 hours | Sunbeam 6 hours |
|---|---|---|---|---|---|---|---|---|
| anatase-type TiO₂ 5 nm | | | | | | | | |
| 0.001% | 0 | Δ | Δ | ○ | ○ | ○ | ○ | ○ |
| 0.01% | 1 | ○ | ○ | ◎ | ◎ | ○ | ◎ | ◎ |
| 0.05% | 5 | ◎ | ◎ | ◎ | ◎ | ○ | ◎ | ◎ |
| anatase-type TiO₂ 5 nm | | | | | | | | |
| 0.06% | 0 | Δ | Δ | ○ | ○ | ○ | ○ | ○ |
| 0.1% | 1 | ◎ | ◎ | ◎ | ◎ | ○ | ◎ | ◎ |
| 1.0% | 5 | ◎ | ◎ | ◎ | ◎ | ◎ | ◎ | ◎ |
| anatase-type TiO₂ 5 nm | | | | | | | | |
| 2.0% | 0 | Δ | Δ | ○ | ○ | ○ | ○ | ○ |
| 5.0% | 1 | ◎ | ◎ | ○ | ◎ | ○ | ◎ | ◎ |
| 10.0% | 5 | ◎ | ◎ | ◎ | ◎ | ◎ | ◎ | ◎ |
| TiO₂ Coated with apatite | | | | | | | | |
| 0.001% | 0 | ○ | ○ | ○ | ○ | ○ | ○ | ○ |
| 0.05% | 1 | ◎ | ◎ | ◎ | ◎ | ○ | ◎ | ◎ |
| 2.0 | 5 | ◎ | ◎ | ◎ | ◎ | ◎ | ◎ | ◎ |
| non | 0 | X | X | X | X | X | X | X |
| | 1 | Δ | Δ | Δ | ○ | Δ | Δ | ○ |
| | 5 | Δ | ○ | ○ | ○ | ○ | ○ | ○ |
| Goods on the market | — | X | Δ | X | X | X | X | X |

What is claimed is:

1. A detergent to be used for washing of a dental resin product, the detergent containing, as a main component, titanium dioxide whose surface has been partly coated with apatite, wherein the apatite is deposited in the form of platy crystals of less than 2 mm in thickness to cover 0.001–10% of the surface of titanium dioxide, and wherein an adjustment agent consisting of acid, peroxide, enzyme or a compound of these components is dispersed and mixed with the titanium dioxide.

2. A detergent of a dental resin product in the form of an aqueous solution in which an adjustment agent consisting of acid, peroxide, enzyme or a compound of these components is dispersed and mixed with titanium dioxide whose surface has been partly coated with apatite, wherein the apatite is deposited in the form of platy crystals of less than 2 mm in thickness to cover 0.001–10% of the surface of titanium dioxide.

3. A detergent of a dental resin product recited in claim 2, wherein apatite hydroxide or phosphoric acid calcium is contained as the apatite.

4. A detergent of a dental resin product as recited in claim 2, wherein anatase-, rutile-, brookite-type titanium dioxide or fine powder of a mixture of these components is contained as the titanium dioxide.

5. A detergent of a dental resin product as recited in claim 2, wherein the mixing ratio of the titanium dioxide partly covered with the apatite to the resin material is adjusted to 0.01–5.00 wt. %.

6. A detergent of a dental resin product as recited in claim 2, wherein a mixture amount of the titanium dioxide partly coated with the apatite is adjusted to 0.01–20 wt. % of the dental resin material.

7. A detergent for a dental resin product as recited in claim 2, wherein the acid mixed with the detergent is selected from a group of consisting of phosphoric acid, pyrophosphric acid, poly-phosphoric acid, tripoly-phosphoric acid, acetic acid, citric acid, tartaric acid, malic acid, formic acid, gluconic acid, silicic acid, succinic acid, oxalic acid, sorbic acid, hydrochloric acid, sulfuric acid, lactic acid, folic acid and butyric acid.

8. A detergent for a dental resin product as received in claim 2, wherein 0.001–10 wt. % of phosphoric acid is used as the adjustment agent.

9. A detergent for a dental resin product as recited in claim 2, wherein 0.01–10 wt. % of sodium pyrophosphoric acid is used as the adjustment agent.

10. A detergent for a dental resin product as received in claim 2, wherein 2.0–7.0 wt. % of hydrogen peroxide is used as the adjustment agent.

* * * * *